(12) United States Patent
Friberg et al.

(10) Patent No.: US 9,827,390 B2
(45) Date of Patent: Nov. 28, 2017

(54) SOUND-PROOFING HOUSING FOR A RESPIRATOR

(71) Applicant: IMT Information-Management-Technology AG, Buchs (CH)

(72) Inventors: Harri Friberg, Mauren (LI); Jakob Daescher, Flaesch (CH)

(73) Assignee: IMT INFORMATION-MANAGEMENT-TECHNOLOGY AG, Buchs (CH)

( * ) Notice: Subject to any disclaimer, the term of this patent is extended or adjusted under 35 U.S.C. 154(b) by 684 days.

(21) Appl. No.: 14/371,076

(22) PCT Filed: Feb. 4, 2013

(86) PCT No.: PCT/IB2013/050930
§ 371 (c)(1),
(2) Date: Aug. 2, 2014

(87) PCT Pub. No.: WO2013/114345
PCT Pub. Date: Aug. 8, 2013

(65) Prior Publication Data
US 2014/0352695 A1    Dec. 4, 2014

Related U.S. Application Data

(60) Provisional application No. 61/594,345, filed on Feb. 2, 2012.

(30) Foreign Application Priority Data

Feb. 2, 2012   (EP) ..................................... 12153645

(51) Int. Cl.
*A61M 16/00*  (2006.01)
*F04D 29/40*  (2006.01)

(52) U.S. Cl.
CPC ....... *A61M 16/0066* (2013.01); *F04D 29/403* (2013.01); *A61M 2205/42* (2013.01)

(58) Field of Classification Search
CPC .................................................. A61M 16/0066
(Continued)

(56) References Cited

U.S. PATENT DOCUMENTS 4,055,173 A * 10/1977 Knab ................. A41D 13/1153
128/201.23
4,195,969 A *  4/1980 Whitney ............... A47L 9/0081
15/412

(Continued)

FOREIGN PATENT DOCUMENTS

DE    19746185 A1    4/1999
DE    10013960 A1    10/2001
(Continued)

OTHER PUBLICATIONS

FinishingIQ, "Dowel insertion equipment vs. fastener insertion equipment"; retrieved from http://www.finishingiq.com/2007/07/31/dowel_insertion_equipment_vs_fastener_insertion_equipment/.*

(Continued)

*Primary Examiner* — (Jackie) Tan-Uyen T Ho
*Assistant Examiner* — Joseph D Boecker
(74) *Attorney, Agent, or Firm* — Nadya Reingand; Yan Hankin

(57) ABSTRACT

Sound-proofing housing (31), which comprises a first housing part (41) having an intake opening (44) and comprises a second housing part (51) having a discharge opening, wherein a shaped part (61) arranged in the housing (31) is also provided, of which the flange seal (63) comes to rest between the housing parts (41, 51) when the housing (31) is put together. The acoustic emission generated by the fan is (Continued)

Figure 1:
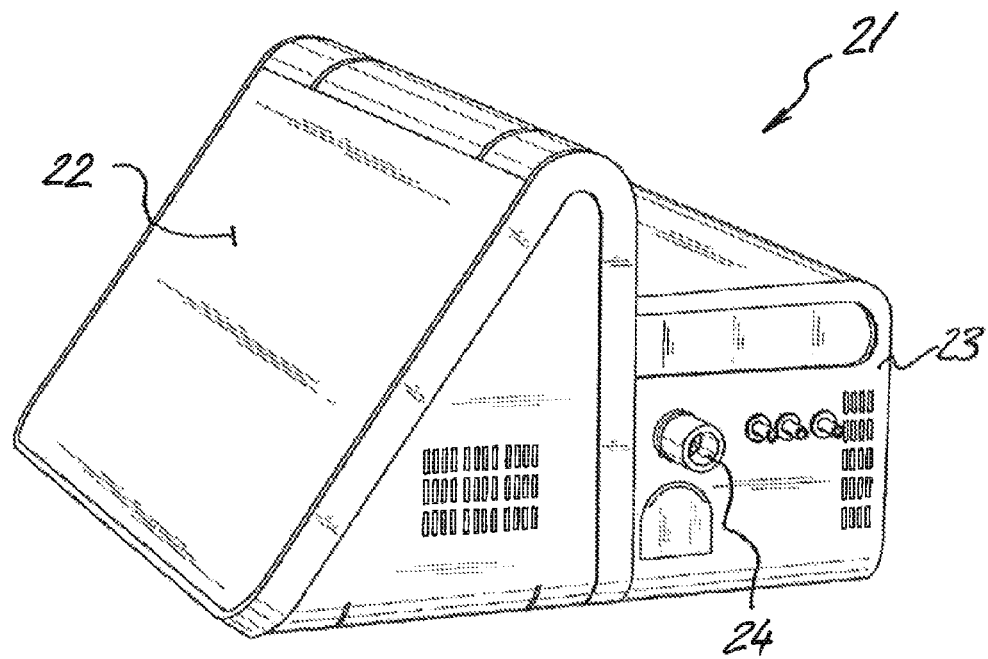

considerably reduced by a specific embodiment of the shaped part (61) with air passage openings and air-guiding devices.

34 Claims, 5 Drawing Sheets

(58) Field of Classification Search
USPC .................................. 128/204.18, 204.21
See application file for complete search history.

(56) References Cited

U.S. PATENT DOCUMENTS

| | | | |
|---|---|---|---|
| 4,794,922 A | 1/1989 | DeVries | |
| 5,694,926 A | 12/1997 | DeVries et al. | |
| 6,216,991 B1 | 4/2001 | Okamoto | |
| 6,474,960 B1 | 11/2002 | Hansmann | |
| 6,571,792 B1 | 6/2003 | Hendrickson et al. | |
| 6,585,662 B1 | 7/2003 | Jones et al. | |
| 6,644,311 B1* | 11/2003 | Truitt | A61M 16/00 128/204.18 |
| 6,837,260 B1* | 1/2005 | Kuehn | A61M 16/0057 128/204.18 |
| 7,212,937 B2 | 5/2007 | Friberg | |
| 7,527,053 B2* | 5/2009 | DeVries | A61M 16/0057 128/204.18 |
| 7,617,823 B2 | 11/2009 | DiMatteo et al. | |
| D620,102 S * | 7/2010 | Klien | D24/110 |
| 7,774,060 B2 | 8/2010 | Westenskow et al. | |
| 7,909,032 B2 | 3/2011 | Feldhahn et al. | |
| 7,975,688 B1 | 7/2011 | Truitt | |
| 8,015,971 B2 | 9/2011 | Kwok | |
| 9,610,416 B2* | 4/2017 | Jones | A61M 16/0066 |
| 2004/0226562 A1* | 11/2004 | Bordewick | A61M 16/0057 128/204.23 |
| 2005/0210622 A1* | 9/2005 | Baecke | A61M 16/0057 15/330 |
| 2007/0193580 A1* | 8/2007 | Feldhahn | A61M 16/00 128/204.18 |
| 2008/0072900 A1* | 3/2008 | Kenyon | A61M 16/0051 128/204.18 |
| 2008/0257346 A1* | 10/2008 | Lathrop | A61M 16/0066 128/204.17 |
| 2008/0304986 A1* | 12/2008 | Kenyon | A61M 16/0066 417/423.12 |
| 2009/0162226 A1* | 6/2009 | Campbell | F04D 29/4226 417/423.14 |
| 2009/0194101 A1 | 8/2009 | Kenyon et al. | |
| 2010/0224190 A1* | 9/2010 | Tilley | A62B 18/006 128/204.21 |
| 2012/0037160 A1* | 2/2012 | Sung | A61M 16/0066 128/205.12 |
| 2012/0138058 A1* | 6/2012 | Fu | A61M 16/0066 128/204.23 |
| 2012/0152255 A1* | 6/2012 | Barlow | A61M 16/0066 128/205.25 |
| 2012/0171058 A1 | 7/2012 | Grasmuck | |
| 2012/0199129 A1* | 8/2012 | Kenyon | A61M 16/0066 128/205.25 |
| 2012/0285454 A1* | 11/2012 | Nibu | A61M 16/0066 128/204.18 |
| 2014/0261422 A1* | 9/2014 | Lang | A61M 16/0051 128/204.21 |
| 2014/0299130 A1* | 10/2014 | Librett | A61M 16/0066 128/204.18 |
| 2014/0299406 A1* | 10/2014 | Librett | A61M 16/0816 181/224 |
| 2014/0332001 A1* | 11/2014 | Bath | A61M 16/00 128/203.27 |
| 2015/0273167 A1* | 10/2015 | Feldhahn | A61M 16/0051 128/204.21 |

FOREIGN PATENT DOCUMENTS

| | | |
|---|---|---|
| DE | 20213232 U1 | 3/2003 |
| DE | 102006034028 A1 | 2/2007 |
| EP | 0669141 A2 | 8/1995 |
| EP | 0669141 A3 | 3/1996 |
| WO | 98/09677 A1 | 3/1998 |
| WO | 2009/067583 A2 | 5/2009 |
| WO | 2009/067583 A3 | 8/2009 |
| WO | 2011/017763 A1 | 2/2011 |

OTHER PUBLICATIONS

International Search Report and Written Opinion of the ISA, dated May 7, 2013 from parent International Application PCT/IB2013/050930 published WO2013/114345A1 on Aug. 8, 2013.
European Search Report and EPO preliminary report on patentability dated Jul. 6, 2012 (in German) from EPO priority application EP12153645 filed Feb. 2, 2012.

* cited by examiner

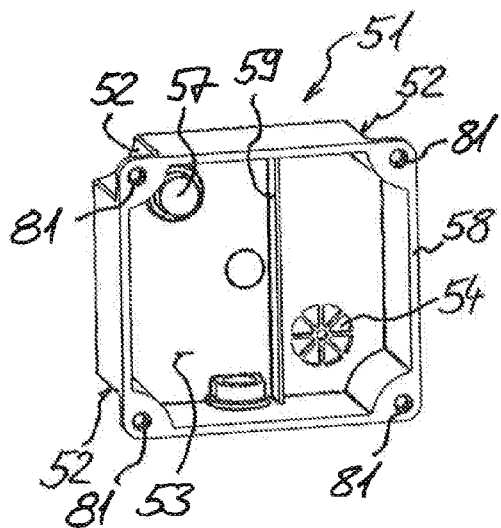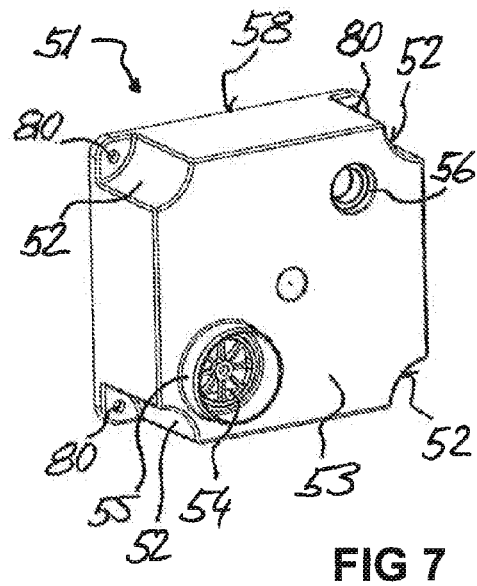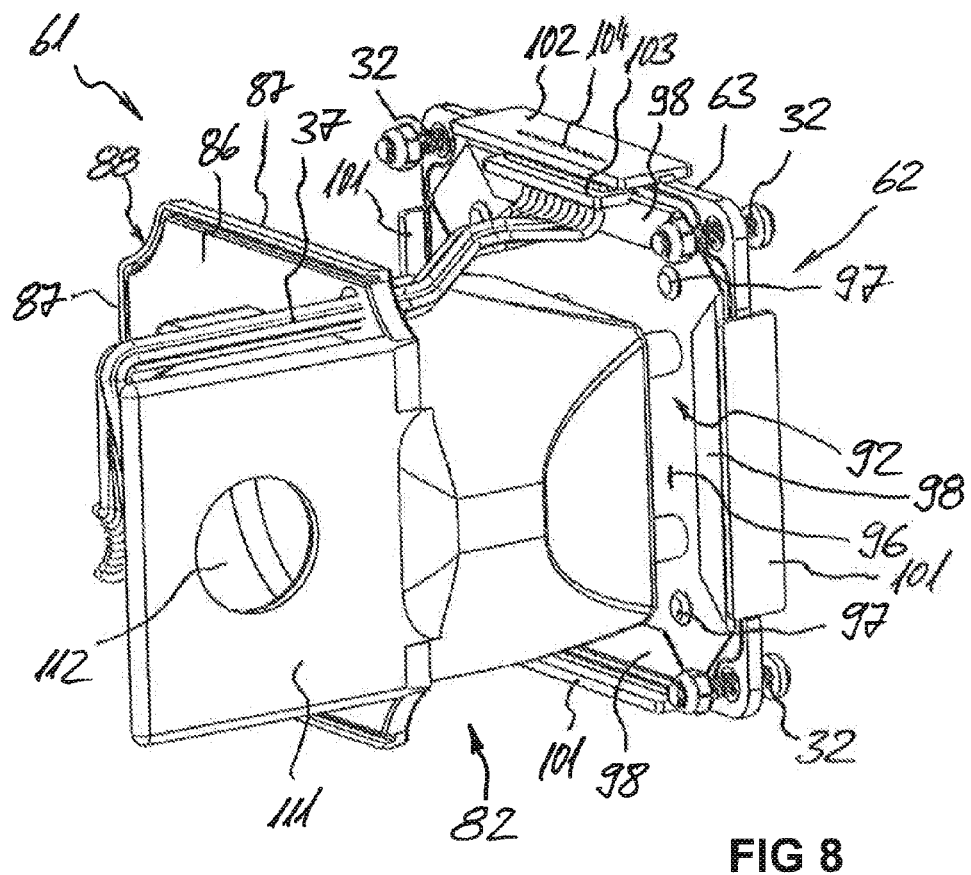

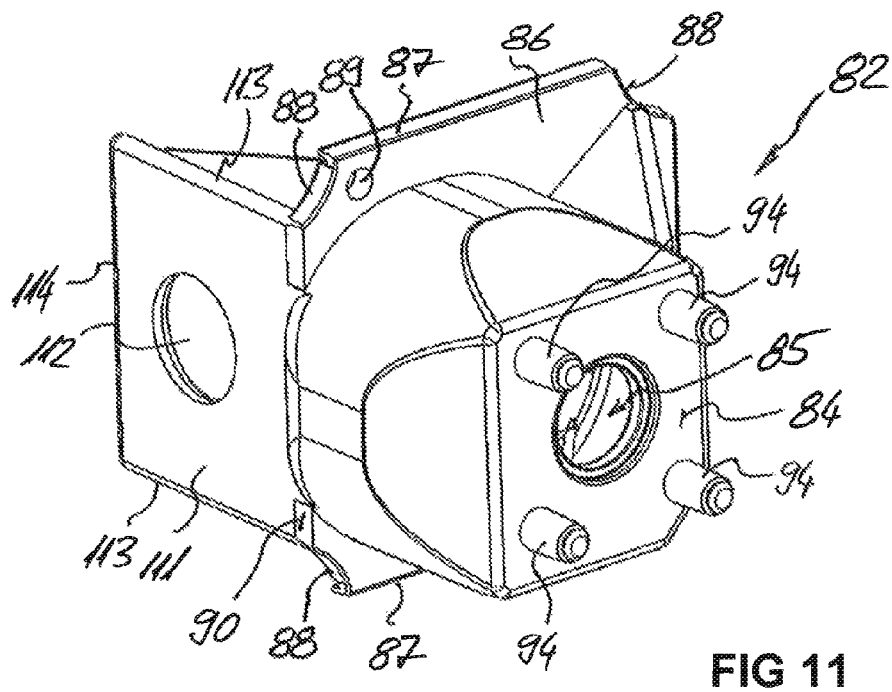
FIG 11
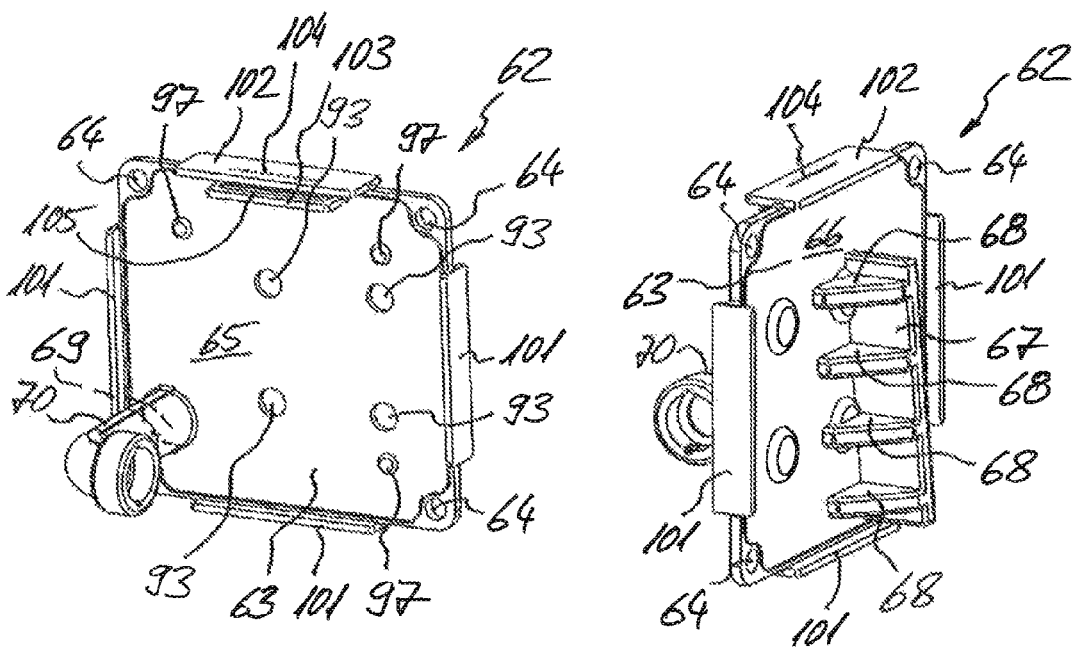
FIG 12
FIG 13

SOUND-PROOFING HOUSING FOR A RESPIRATOR

This application is a 35 U.S.C. 371 national-phase entry of PCT International application no. PCT/IB2013/050930 filed on Feb. 4, 2013 and also claims benefit of priority to prior European application no. EP12153645 filed on Feb. 2, 2012, and also claims priority as a non-provisional of U.S. provisional application Ser. No. 61/594,345 filed on Feb. 2, 2012, and both European application no. EP12153645 and U.S. provisional application Ser. No. 61/594,345, as well as parent PCT International application no. PCT/IB2013/050930, are all incorporated herein by reference in their entireties for all intents and purposes, all as if identically set forth in full herein.

The invention relates to a sound-proofing for a respirator. The invention further relates to a respirator comprising such a sound-proofing housing.

A respirator is used to assist a patient when breathing or to take over fully the breathing function. To this end, a fan, which draws in air in an accordingly controlled manner, compresses said air and then provides the compressed air to the patient at a correspondingly high pressure, is normally provided in the respirator. The delivery opening of the respirator is connected via a feed line to a respiratory mask for example, which is fitted on the patient.

The fan, also referred to as an air generator, for example comprises a motor, for example an electric motor, and a compressor driven by the motor, for example an impellor or a turbine. Noise is generated during operation of the fan, both by the fan itself and also by the airflow, and is bothersome for the patient and also for the carers, in particular in the event of a long period of use of the respirator.

There was thus a need to reduce the noise level, in particular in the case of respirators, during operation thereof.

For a ventilation, heating or air-conditioning system of a motor vehicle, it is proposed for example in DE19746185A1, which is foreign to the classification in question, to provide a separate holder for the fan motor, wherein resiliently yielding support elements directly supporting the motor are provided to decouple vibrations between the motor and the holder.

With this known solution, vibrations generated directly by the fan motor are indeed damped, but the noise level during operation of the ventilation, heating or air-conditioning system only falls to an inconsiderable extent. Since, during operation of a motor vehicle, further loud noises are produced, the reduction in acoustic emission of the ventilation, heating or air-conditioning system achieved by this solution is sufficient for this purpose. The reduction in acoustic emission achievable by this solution is insufficient for a respirator.

WO2009/067583A2 shows a modular powered air purifying respirator comprising a housing having an upper body which has an inlet for the entry of air into the housing. Said air being drawn in by a fan arranged in the housing. The housing has also a lower body which has an outlet for the discharge of the drawn-in air from the housing. Furthermore said housing also comprises a lower body cover arranged in the housing which forms an enclosed space to create a sealed breathing zone that is in fluid communication with the inlet and the outlet. A holder for the motor of the fan is positioned within the sealed breathing zone. This holder encircles the fan, has a fan receptacle and is located between the fan and the lower body. The fan receptacle protrudes from the delivery side facing the delivery region. Air-guiding devices for guiding the air drawn-in by the fan are provided within the housing.

This known solution has comparable disadvantages as pointed out in respect to DE19746185A1, mainly still loud noise. In the normal use of such an air purifying respirator (shown in the FIGS. 9 and 10 of WO2009/067583A2) the reduction in acoustic emission of the air purifying respirator achieved by this solution is sufficient for this purpose. The reduction in acoustic emission achievable by this solution is insufficient for a respirator which is used in hospital or by a patient.

It is proposed in DE20213232U1 to provide a sound-proofing housing for receiving a fan turbine, said housing consisting of two fully closable chambers. The first chamber has an air intake opening and receives the turbine, which delivers the compressed air into the second chamber having the air outlet opening. Both chambers have a foam lining on all chamber walls. The first chamber additionally has a discharge opening, in which the drive motor of the turbine is resiliently mounted.

A disadvantage of this known solution is that the sound-proofing housing requires a large amount of space in a respirator and thus only allows a compact embodiment of the respirator to a limited extent. In addition, this sound-proofing housing requires a high assembly effort.

A respirator is known from U.S. Pat. No. 7,617,823B2, in which the fan is arranged in a receptacle of a shaped part made of a resilient material, which is inserted into a first housing part of the respirator. The shaped part additionally has air-guiding channels. To fix the fan in the first housing part, a further damping insert and a cover element, which covers said damping insert and is screwed to the first housing part, are provided.

A disadvantage of this known solution is that the sound-proofing requires a large amount of space compared to the desired compact dimensions of the respirator, and the assembly of the respirator is very complicated due to the complexity of this solution. Furthermore, the fan and the components thereof are not cooled sufficiently for long periods of use.

It is proposed in U.S. Pat. No. 7,975,688B1 to arrange the fan between two damping elements, which are fixed by means of a cover element on a component, which is arranged in the respirator.

The disadvantage of this known solution is that the assembly of the respirator is very complicated due to the complexity and the soundproofing is insufficient in practice due to the constructional embodiment. With this solution too, the fan and components thereof are only cooled insufficiently.

DE102006034028A1 discloses a sound-proofing housing for a respirator, said housing comprising a first housing part with an intake opening for the entry of air into the housing, said air being drawn in by a fan arranged in the housing, and comprising a second housing part, which comprises a discharge opening for the discharge of the drawn-in air from the housing. A shaped part arranged in the housing is also provided and comprises a flange seal, which comes to rest between the first housing part and the second housing part when the housing is put together and divides the housing into an intake region and a delivery region, and comprises a fan receptacle for holding the fan in the housing, said receptacle protruding from the intake side of the flange seal. Air-guiding devices for guiding the air drawn in by the fan are also provided within the housing in the shaped part.

A disadvantage of this known solution is that the sound-proofing housing requires a large amount of space compared to the desired compact dimensions of the respirator, and assembly of the respirator is also complicated. In this case the cooling of the fan and components thereof is likewise sub-optimal.

The object of the present invention is therefore to create a sound-proofing housing for a respirator that does not have the above-mentioned disadvantages and in particular is of simple design so as to simplify the assembly of the housing. In addition, optimal soundproofing during operation of the fan or the respirator is to be ensured, even in the most confined of spaces.

Advantageous developments are presented in the figures and in the present disclosure.

In accordance with the invention, a support flange, which comprises at least one air passage opening for the air drawn in by the fan as well as contact sides contacting the inner side of a housing part when the housing is put together, is provided in the region of the free end of the fan receptacle, and at least one further air passage opening for the air drawn in by the fan is provided in the fan receptacle, preferably adjacent to the intake side of the flange seal.

The shaped part comprising the fan receptacle can be inserted as a whole into a housing part, until the flange seal contacts the corresponding free edge of the housing part. The support flange distanced from the flange seal comes into contact with the inner sides of the housing part and aligns the shaped part in the desired position within the housing, even as said shaped part is being introduced. It is thus ensured in the simplest manner possible that the fan arranged in the substantially sleeve-shaped fan receptacle is completely decoupled from the housing. The other housing part is then arranged so that the shaped part is securely fixed due to the flange seal fixed between the housing parts.

The air drawn in by the fan passes through the intake opening and into the housing, flows through the air passage opening in the support flange past the fan receptacle, and flows through the further air passage opening in the fan receptacle into the fan. This air is compressed in the fan and is delivered through the discharge opening. A sufficient clearance for the air flowing through the housing is created around the advantageously sleeve-shaped fan receptacle and ensures sufficient and advantageous cooling of the fan and in particular of the drive motor thereof.

The sound-proofing housing according to the invention is characterised by a particularly high ease of assembly with a compact embodiment. At the same time, a long period of use of the fan and therefore of the respirator is ensured.

Seal elements are preferably provided on the contact sides of the support flange and prevent an infiltration of air into the contact regions between the contact sides of the support flange and the corresponding inner sides of the housing. The seal elements are advantageously formed as preferably resilient lip seals. Due to the embodiment and positioning of the at least one air passage opening in the support flange, the flow behaviour and therefore in particular also the efficiency of the cooling effect for the fan can be influenced significantly. The seal elements ensure the desired guidance of air within the housing, even in the event of vibrations produced in any case by the operation of the fan.

An intake-side guide element having at least one air passage opening preferably protrudes in the form of an air-guiding device from the support flange and ensures that the airflow is steered within the housing in an advantageous manner in the intake region of the sound-proofing housing. The intake-side guide element is particularly advantageously arranged in the vicinity of, or directly adjacent to, the air passage opening in the support flange. The size of the cross section of the air passage opening advantageously corresponds approximately to 0.8 times to 1.2 times the size of the air passage opening in the support flange.

At least one support portion for the intake-side guide element is preferably provided and ensures the desired alignment of the intake-side guide element within the housing. The at least one support portion advantageously extends from the intake-side guide element to the support flange, which ensures stable support of the intake-side guide element. In spite of the forces that are effective due to the airflow within the housing, the intake-side guide element itself may have a low material thickness. A reduction in the material requirement for the shaped element has an advantageous effect in particular on the production costs and also the handling of the shaped element. At least two support portions for the intake-side guide element are advantageously provided and are arranged at a distance from one another and ensure that the intake-side guide element is aligned in an even more stable manner. For advantageous support of the intake-side guide element, the support portions are each preferably provided adjacent to the two free side edges, running parallel to one another, of the intake-side guide element.

At least one guide receptacle for receiving a portion of the intake-side guide element is preferably provided in the housing part in which the intake-side guide element comes to rest when the housing is put together. The at least one guide receptacle is advantageously formed in such a way that, as the shaped element is introduced into the corresponding housing part, the free ends of the intake-side guide element are surrounded by the shaped element, at least in some regions. Due to the at least one guide receptacle stabilising the intake-side guide element, the intake-side guide element can have a low material thickness in spite of the forces that are effective due to the airflow within the housing.

At least two mutually opposed guide receptacles are particularly advantageously provided and hold the intake-side guide element at the two free side edges thereof running parallel to one another. In addition, the arrangement of a further guide receptacle, which holds the free edge at the end of the intake-side guide element, at least in some regions, is also advantageous.

In a preferred embodiment, the intake-side guide element is fixed in the housing in the desired alignment by means of at least one guide receptacle and also by means of at least one support portion.

One housing part preferably comprises at least one fastening dome protruding from the free edge of the housing part, and the other housing part preferably comprises at least one fastening dome recess for receiving the at least one fastening dome when the housing is put together, so that, when the two housing parts are put together, they are aligned with one another during the assembly process. If the housing parts are asymmetrical in cross section, the correct alignment of the housing parts relative to one another can be ensured in a simple manner by a corresponding arrangement of the at least one fastening dome and the at least one fastening dome recess. A plurality of fastening domes and a corresponding number of fastening dome recesses are advantageously provided.

A stop for the at least one fastening dome is advantageously provided in the fastening dome recess to ensure a defined spacing between the housing parts when the housing is put together, whereby in particular an undesirably heavy compression of the flange seal of the shaped part coming to rest between the housing parts is prevented in a simple manner.

At least one dome through-opening for the passage of the at least one fastening dome is preferably provided in the flange seal, whereby the flange seal and therefore the shaped part are held in the desired alignment relative to the housing parts. The number of dome through-openings in the flange seal advantageously corresponds at least to the number of the fastening domes provided on the corresponding housing part. In this case too, a desired alignment of the shaped part in the housing can be ensured in a simple manner by a corresponding arrangement of the dome through-openings adapted to the geometrical conditions.

The at least one dome through-opening is advantageously peripherally closed, which reliably prevents an undesired displacement of the flange seal and therefore of the entire shaped part when the sound-proofing housing is put together.

A delivery-side guide element is preferably provided in the form of an air-guiding device on the flange seal and protrudes from the delivery side of the flange seal, which is arranged opposite the intake side of the flange seal, which ensures that the airflow is steered within the housing in an advantageous manner in the delivery region of the sound-proofing housing.

At least one support portion for the delivery-side guide element is advantageously provided and ensures the desired alignment of the delivery-side guide element within the housing. The at least one support portion advantageously extends from the delivery-side guide element to the flange seal, which ensures stable support of the delivery-side guide element. In spite of the forces that are effective due to the airflow in the housing, the delivery-side guide element itself can have a low material thickness. As has already been explained, a reduction of the material requirement for the shaped element in particular has an advantageous effect on the production costs and also the handling of the shaped element. A plurality of support portions for the delivery-side guide element are advantageously provided and are arranged at a distance from one another and ensure that the delivery-side guide element is aligned in a more stable manner. For advantageous support of the delivery-side guide element, the support portions are preferably each provided adjacent to the two free side edges, running parallel to one another, of the delivery-side guide element.

At east one cable through-opening for the passage of cables for the wiring of the fan is preferably provided in the flange seal, which enables a simple seal against false air and against an air short circuit and simultaneously enables simple wiring of the fan.

The at least one cable through-opening is advantageously provided in an encompassing portion, which protrudes from the flange seal, which enables simple constructional assembly that does not make it difficult to put the housing together.

A housing recess for receiving at least one region of the encompassing portion is further advantageously provided in the housing part in which the encompassing portion comes to rest when the housing is put together, which enables accurate, fault-free constructional assembly of the housing and at the same time creates sufficient clearance for the wiring.

At least one cable through-opening for the passage of cables for the wiring of the fan is preferably provided in the support flange and/or in the intake-side guide element so that the corresponding cables for the fan are securely guided and held within the housing. Damage to the cables is thus prevented, even in the event of strong airflows within the housing.

At least one air passage opening, through which the air compressed by the fan can flow from the intake region into the delivery region, is preferably provided in the flange seal. The at least one aft passage opening is advantageously spaced from the edge of the flange seal so that it is surrounded peripherally by material of the flange seal. The desired seal in the region of the flange seal is maintained, even under high forces produced for example by the airflow.

A line portion (for example a "swan-neck") is advantageously provided and connects the air passage opening to a delivery-side outlet (for example the outlet connecting piece) of the fan, whereby an air short circuit between drawn-in air and compressed air is prevented.

A support element for supporting the flange seal is preferably provided and ensures the desired alignment of the flange seal within the housing. In spite of the forces that are effective due to the airflow, the flange seal itself may have a low material thickness. As has already been explained above, a reduction of the material requirement for the shaped element in particular has an advantageous effect on the production costs and also the handling of the shaped element. The support element is advantageously fabricated from a rigid material, for example from sheet metal or a suitable plastics material. The dimensions are advantageously selected in such a way that, when the sound-proofing housing is put together, said support element comes to rest completely within the corresponding housing part. The support element further advantageously comprises contact portions, which protrude and extend from the plane spanned by the flange seal and can be used to support the inner wall of the corresponding housing part. Displacement of the shaped part in this region is thus limited to the resultant play predetermined by the construction. The support element is advantageously arranged on the intake side of the flange seal, which enables simple assembly of the shaped part and therefore of the housing as a whole.

The shaped part is preferably formed at least in two parts, wherein a first shaped part portion comprises at least the flange seal and the at least one further shaped part portion comprises at least the fan receptacle, wherein a fixing device for connecting the first shaped part portion to the at least one further shaped part portion is provided. A shaped part formed in this way can be fabricated in a simple manner. In particular if the shaped part is a part that is injection-moulded or foamed in a mould, the corresponding mould can thus be designed more simply than in the case of a one-pieced shaped part. The mould can thus be produced more favourably, and demoulding of the produced portion of the shaped part is considerably simplified.

The fixing device preferably comprises at east one fixing cam provided on one of the shaped part portions and at least one fixing cam receptacle provided on the other shaped part portion, the at least one fixing cam being fixable in said fixing cam receptacle, which enables a simple connection of the at east two shaped part portions.

For example, a groove for engagement from behind distanced from the free end of the at least one fixing cam is provided on said at least one fixing cam and the at least one fixing cam receptacle has inner dimensions matched to the dimensions of the groove for engagement from behind or smaller than the corresponding dimensions of the free end of the at least one fixing cam. When joining the shaped part portions, the corresponding part of the fixing cam receptacle snaps into the groove for engagement from behind, whereby the shaped part portions are securely interconnected.

The fixing device is advantageously formed in such a way that, when the shaped part portions have been joined, they are spaced from one another, at least in some regions, so that an intake gap for the air drawn in by the fan remains in the form of at least one further air passage opening. The desired air guidance can be ensured with little effort by means of this embodiment, without a complicated embodiment of the mould for producing the corresponding shaped part portion.

Further advantages, features and details of the invention will emerge from the following description, in which exemplary versions are described with reference to the drawings.

The list of reference signs forms part of the disclosure. The drawings will be described coherently and comprehensively. Like reference signs denote like components.

Figure 2:
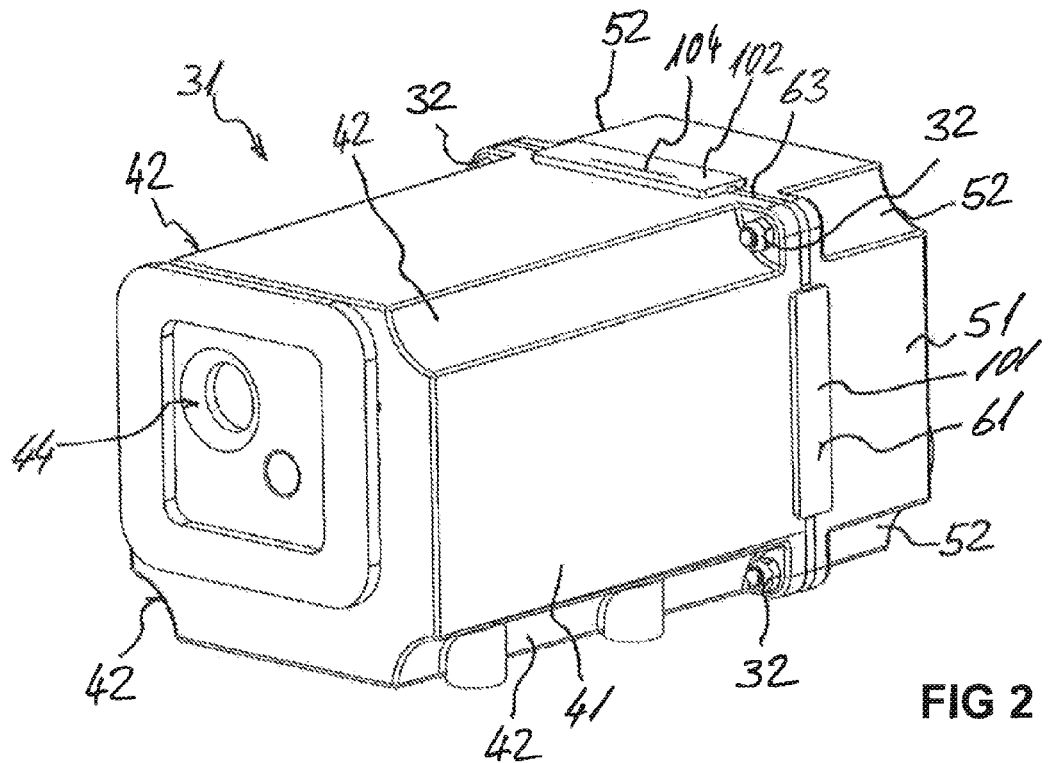
Figure 3:
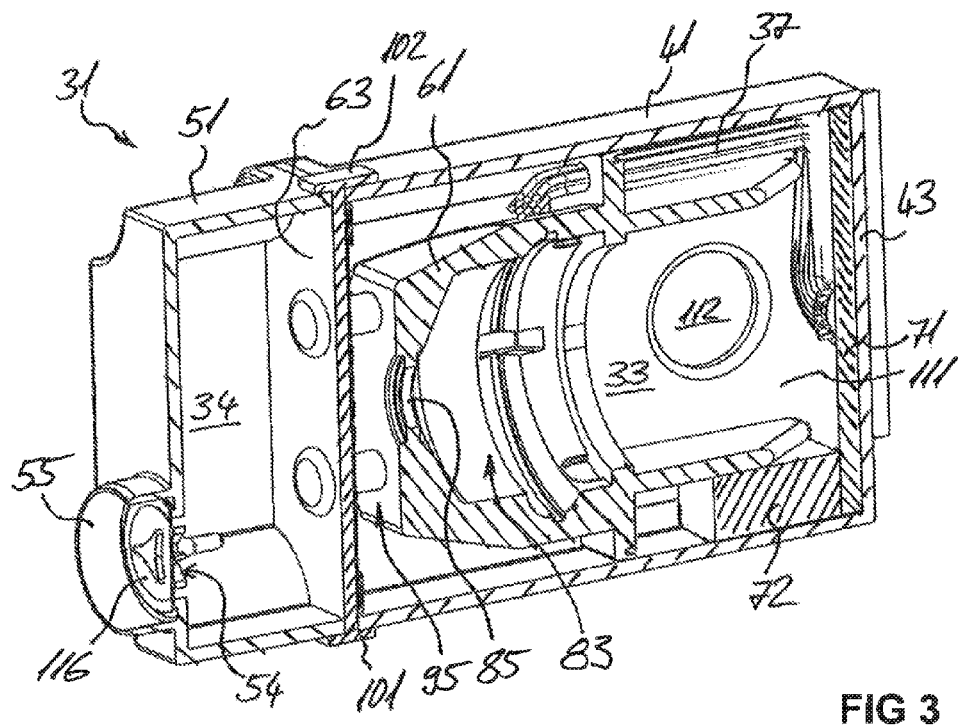
Figure 4:
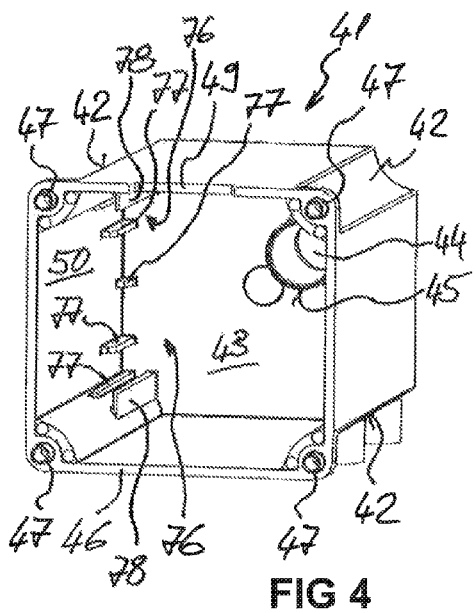
Figure 5:
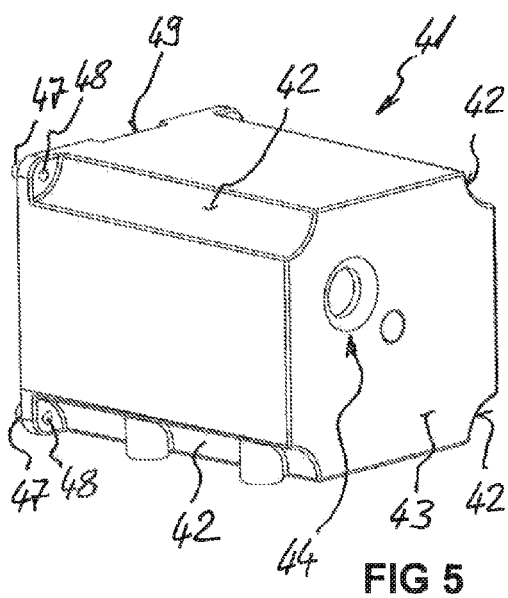
Figure 9:
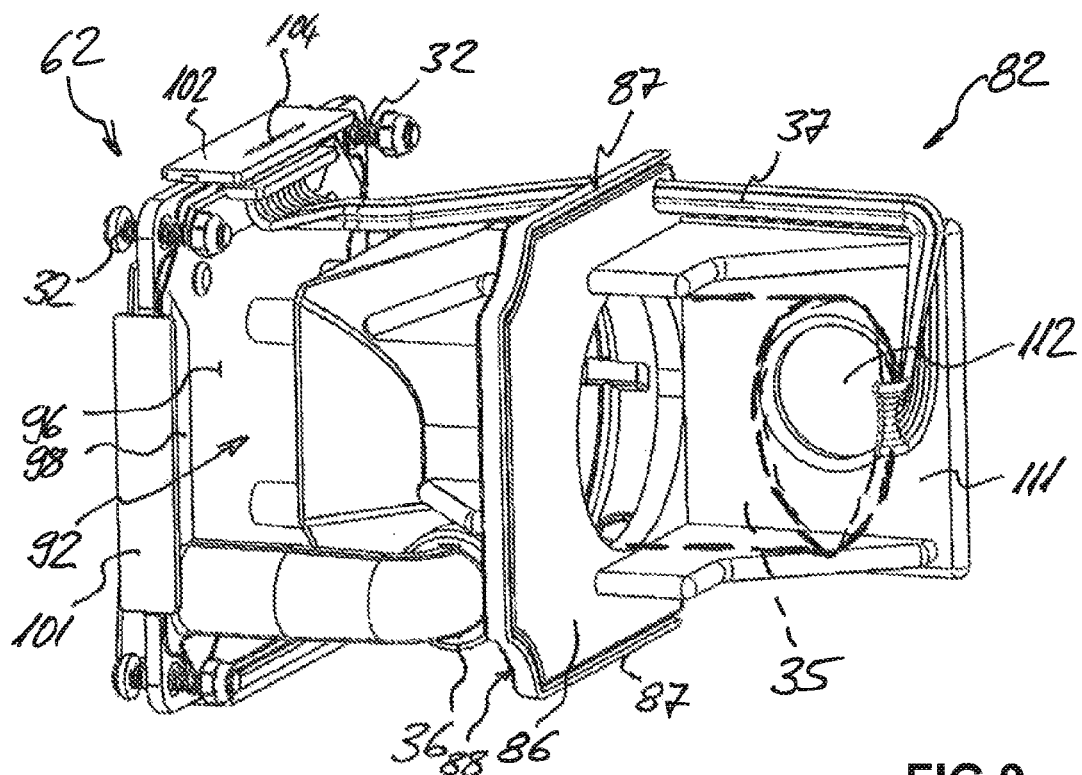
Figure 10:
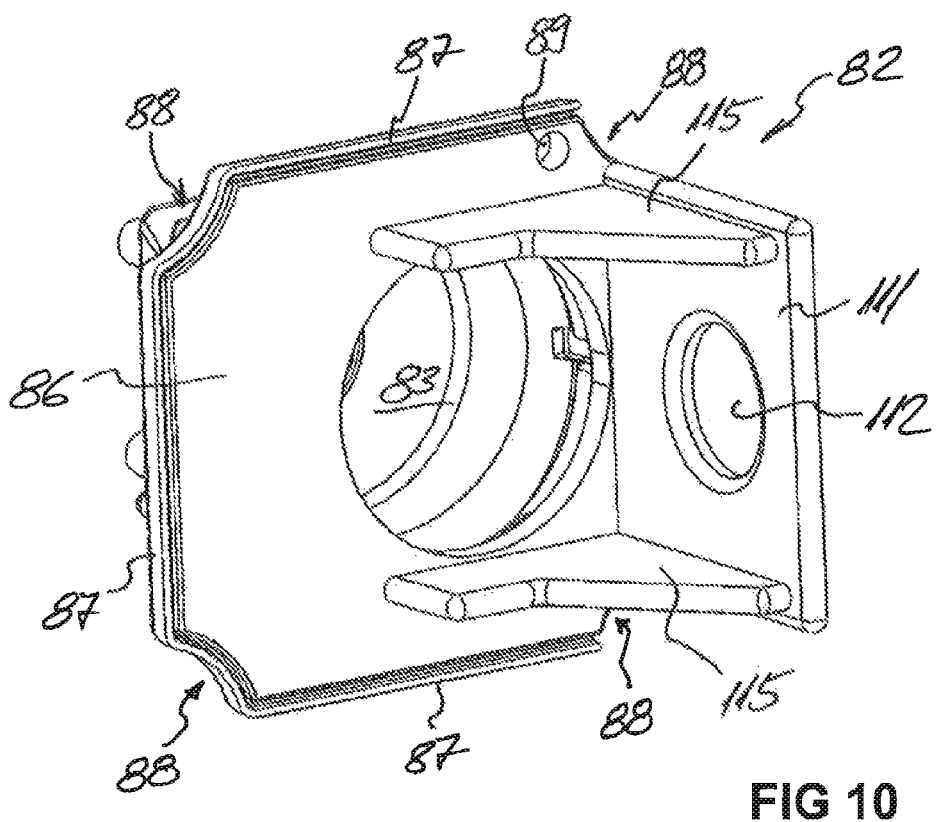

In the drawings:

FIG. 1 shows a perspective illustration of a respirator,

FIG. 2 shows a perspective illustration of a sound-proofing housing according to the invention for the respirator, FIG. 3 shows a longitudinal section through the sound-proofing housing, FIG. 4 shows a perspective illustration of a first housing part of the sound-proofing housing, FIG. 5 shows another perspective illustration of the first housing part according to FIG. 4, FIG. 6 shows a perspective illustration of a second housing part of the sound-proofing housing, FIG. 7 shows another perspective illustration of the second housing part according to FIG. 6, FIG. 8 shows a perspective illustration of a shaped part of the sound-proofing housing, FIG. 9 shows another perspective illustration of the shaped part according to FIG. 8, FIG. 10 shows a perspective illustration of a first portion of the shaped part according to FIGS. 8 and 9, FIG. 11 shows another perspective illustration of the first shaped part portion according to FIG. 10, FIG. 12 shows a perspective illustration of a second portion of the shaped part according to FIGS. 8 and 9, and FIG. 13 shows another perspective illustration of the second shaped part portion according to FIG. 12.

A respirator 21, as is shown in FIG. 1, is used to assist a patient's breathing or to take on fully a patient's respiratory function. Parameters matched to the patient can be input via an input unit, for example a touchscreen 22. A processor/control unit (not illustrated here), which ensures the desired type of respiration for the patient by controlling accordingly a fan provided in the housing 23, is located within the housing 23. A connecting piece 24, to which a respiration tube (not illustrated here) for guiding air from the respirator 21 to a respiratory mask for patient respiration, is provided on the housing 23. The market for respirators 21 requires a compact design and low acoustic emission, in particular of the fan provided in the respirator 21.

A sound-proofing housing 31 according to the invention for a fan is illustrated in FIGS. 2 to 13, said housing being of compact construction and demonstrating advantageous soundproofing alongside simple production and ease of assembly of the housing 31. Such a housing 31 is advantageously arranged in a respirator 21, as is shown in FIG. 1, to generate the desired airflow for patient respiration.

FIG. 2 shows the sound-proofing housing 31 as a whole when put together. The housing 31 comprises a first cup-shaped housing part 41, a second cup-shaped housing part 51, and a shaped part 61 that is arranged in the housing 31 and of which substantially only the flange seal 63 arranged between the two housing parts 41 and 51 can be seen in FIG. 2.

The housing parts 41 and 51 are interconnected in the region of four corners by means of connecting elements 32, such as screws and nuts. For easy accessibility of the connecting elements 32 and therefore for simple assembly of the housing 31, the first housing part 41 comprises correspondingly formed depressions 42 along its longitudinal extension, and the second housing part 51 comprises correspondingly formed depressions 52 along its longitudinal extension.

It can be seen from FIG. 3 that, besides the shaped part 61, foam inserts 71 and 72 are provided in the region of the base portion 43 of the first housing part 41 and, additionally to the shaped part 61, in particular damp noise in the housing 31 produced by the airflow. It can also be seen here that the shaped part 61 and in particular the flange seal 63 thereof divides the interior of the housing 31 into an intake region 33 and into a delivery region 34.

The features of the first cup-shaped housing part 41 will be described hereinafter with reference to FIGS. 4 and 5. An intake opening 44 for the entry of air into the housing 31 is provided in the base portion 43 of the first housing part 41. The intake opening 44 has a cross section that tapers from the outer side of the base portion 43. This cross section tapers to an inner diameter of a substantially cylindrical sleeve portion 45, which protrudes from the base portion 43 into the first housing part 41. The tapering region of the intake opening 44 runs in a rounded manner. This embodiment of the intake opening 44 ensures an advantageous airflow into the housing 31 and also ensures that the acoustic emissions when the air flows into the housing 31 are considerably reduced.

Fastening domes 47 each protruding from the free edge 46 are provided in the corner regions of the free edge 46 of the first housing part 41. Through openings 48 for at least part of the connecting element 32 are provided in each fastening dome 47 and each fully penetrate the corresponding fastening dome 47.

A housing recess 49, of which the function will be described hereinafter in conjunction with the shaped part 61, is also provided in a portion of the free edge 46 of the first housing part 41.

Furthermore, two guide receptacles 76 (FIG. 3), of which the function will likewise be described hereinafter in conjunction with the shaped part 61, are provided inside the first housing part 41. Each guide receptacle 76 is formed by at least one of the plurality of ribs 77 and a retaining tab 78. Each of the ribs 77 protrude perpendicularly from the corresponding side wall 50 of the first housing part 41 and extend, starting from the base portion 43, over regions in the direction of the free edge 46 of the first housing part 41. As can be seen in FIG. 3, the individual ribs 77 may extend over different lengths. The retaining tabs 78 are each arranged substantially at the same distance from the inner side 50 of the first housing part 41 and run, starting from the base portion 43, in the direction of the free edge 46 of the first housing part 41. The free ends of the retaining tabs 78 each face one another. The length of the extension of the retaining tabs 78 is advantageously greater than the corresponding extension of the ribs 77. Furthermore, the ribs 77 and/or the retaining tabs 78 do not necessarily have to be connected to the corresponding inner face of the base portion 43. All of these ribs and/or retaining tabs, or at least individual ones thereof, may readily be spaced from the corresponding inner face of the base portion 43.

The features of the second cup-shaped housing part 51 will be described hereinafter with reference to FIGS. 6 and 7. A discharge opening 54 for the discharge of the drawn-in air from the housing 31 is provided in the base portion 53 of the second housing part 51.

A collar 55 protrudes around the discharge opening 51 from the outer side of the base portion 53. The outer diameter of the collar 55 is advantageously selected in such a way that, with an arrangement of the housing 31 in the respirator 21, this collar 55 comes to rest in the connecting piece 24 of the respirator 21. Struts running radially from the centre of the discharge opening 54 are also provided in said discharge opening and are used as a support for a membrane 116 (FIG. 3), such that a check valve is formed at the discharge opening 54.

A relief opening 56, in which a pressure relief valve 57 for example is arranged, is further provided in the base portion 53 of the second housing part 51. In the event of an excessive pressure within the housing 31, this pressure can escape through said relief opening 56. An undesirably high overpressure can build up within the housing 31 for example if no air is drawn by the patient, but the fan 35 continues to compress drawn-in air. To improve the stability of the second housing part 51, a reinforcing rib 59 running from one side wall to the opposite side wall of the second housing part 51 is also provided on the inner side of the base portion 53, wherein the discharge opening 54 is arranged on one side of the reinforcing rib 59 and the discharge opening 56 is arranged on the other side of the reinforcing rib 59.

Fastening dome recesses 81 for receiving the fastening domes 47 of the first housing part 41 are provided in the corner regions of the free edge 58 of the second housing part 51. The fastening dome recesses 81 are each penetrated by through-openings 80 for at least part of the connecting element 32. The inner diameter of a fastening dome recess 81 is greater than the inner diameter of the corresponding through-opening 80, so that a stop for the fastening dome 47 received in said fastening dome recess 81 is formed in the fastening dome recess 81 to ensure a defined spacing between the free edges 48 and 58 of the housing parts 41 and 51 when the housing 31 is put together.

FIGS. 8 and 9 show the shaped part 61 as a whole. The de ails of the shaped part 61 and the individual functions thereof will be described hereinafter with reference to FIGS. 10 to 13.

The shaped part 61 consists of a first shaped part portion 62 and a second shaped part portion 82, which are interconnected via a fixing device 92. The shaped part 61 and therefore the shaped part portions 62 and 82 are fabricated for example from a plastics material, advantageously from silicone, NBR, FKN or a suitable elastomer. In this case the two shaped part portions 62 and 82 do not necessarily have to be fabricated from the same material, although this is generally advantageous.

The first shaped part portion 62 (in particular see FIGS. 12 and 13) comprises the flange seal 63. A peripherally dosed dome through-opening 64 for the passage of a respective fastening dome 47 of the first housing part 41 is provided in each corner region of the flange seal 63.

Fixing cam receptacles 93, which form a part of the fixing device 92, are provided on the intake side 65 of the flange seal 63. Retaining cams 97, which are used to hold a support element 96 for supporting the flange seal 63, also protrude from the intake side 65 of the flange seal 63 (FIG. 8). The support element 96 fabricated from a sheet metal comprises, at its side edges, deflected portions 98, which, when the support element 96 is fixed, protrude in a manner facing away from the intake side 65. The size of the support element 96 is selected in such a way that, when the housing 31 is put together, the support element 96 comes to rest via its deflected portions 98 within the first housing part 41.

A delivery-side guide element 67, which runs parallel to the side edges of the flange seal 63 and of which each of the ends are spaced from said side edges, protrudes in the form of an air-guiding device from the delivery side 66 of the flange seal 63, which is arranged opposite the intake side 65 of the flange seal 63. When the housing 31 is put together, the free edge of the delivery-side guide element 67 facing the base portion 53 of the second housing part 51 and the free edge of the reinforcing rib 59 in the second housing part 51 are arranged facing one another so that a narrowed air passage region is created therebetween. A plurality of support portions 68 for the delivery-side guide element 67 each spaced from one another and from the ends of the delivery-side guide element 67 are provided and extend from the delivery-side guide element 67 to the flange seal 63.

With reference to FIG. 13, an air passage opening 69 spaced from the side edges of the flange seal 63 is provided after the delivery-side guide element 67 in the flange seal 63, which connects the intake region 33 of the housing 31 to the delivery region 34 thereof, and therefore is not visible in this figure. A guide portion 70 with a curved free end is provided on the intake side 65 of the flange seal 63 and connects the air passage opening 69 to an outlet 36, advantageously formed as a connecting piece, of the housing 35 and thus prevents an air short circuit between the intake region 33 and the delivery region 34.

An encompassing portion 101 and 102 is provided on each side edge of the flange seal 63 and extends along the flange seal 63 in a manner distanced from the ends of the corresponding side edge of the flange seal and substantially perpendicular to the plane spanned by the flange seal 63 and over the intake side 65 and the delivery side 66 of the flange seal 63. The encompassing portions 101 and 102 come to rest outside the two housing parts 41 and 51 when the housing 31 is assembled (for example see FIG. 2).

A guide portion 103, which, when the housing 31 is put together, comes to rest within the first housing part 41, is provided on the inner side of the encompassing portion 102 at a distance therefrom. A cable through-opening 104 for the passage of cables 37 for the wiring of the fan 35 is provided in the encompassing portion 102. The cable through-opening 104 is formed in such a way that the edges thereof bear tightly against the cable 37 guided therethrough and prevent an infiltration of moisture and/or dirt into the housing 31. The guide portion 103 comprises a guide through-opening 105 for the cable 37.

When the shaped part 61 is put together with the first housing part 41, at least one region of the encompassing portion 102 and therefore also the cable 37 in the housing recess 49 guided through the cable through-opening 104 comes to rest on the free edge 46 of the first housing part 4 so that said cable 37 is not damaged during the assembly process and simple assembly of the housing 31 is also ensured.

The second shaped part portion 82 comprises a substantially cup-shaped fan receptacle 83 for holding the fan 35 in the housing 31. The fan receptacle 83 comprises a base portion 84 having an air passage opening 85, which, when fixed on the first shaped part portion 62, faces the intake side 65 of the flange seal 63. At the free end remote from the intake side 65 of the flange seal 63, the fan receptacle 83 comprises a support flange 86 surrounding said fan receptacle, at least in some regions. The support flange 86 comprises three contact sides contacting the inner side of the first housing part 41 when the housing 31 is put together. Lip seals 87 are provided as seal elements on these contact sides of the support flange 86. Recesses 88 are formed in each of the corners of the support flange 86 and ensure tight contact against the accordingly rounded inner sides of the first housing part 41 when the housing 31 is put together. The lip seals 87 advantageously also extend along the recesses 88. A cable through-opening 89 for the passage of cables 37 for the wiring of the fan 35 is also provided in the support flange 86.

A plurality of fixing cams 94 protrude in the form of a further part of the fixing device 92 from the base portion 84, the free ends of said fixing cams being fixable in the fixing cam receptacles 93 in the flange seal 63 to connect the first shaped part portion 62 to the second shaped part portion 82. This fixing process is carried out for example via a clip device or by means of a suitable adhesive.

The fixing device 92 or the fixing cams 94 is/are formed in such a way that, when the two shaped part portions 62 and 82 are joined, they are distanced from one another. An intake gap 95 thus remains adjacent to the intake side 65 of the flange seal 63 as a further air passage opening for the air drawn in by the fan 35.

In the case of the side edge 90 of the support flange 86, which, when the housing 31 is put together, does not contact one of the inner sides of the first housing part 41, an intake-side guide element 111 having an air passage opening 112 protrudes from the support flange 86, more specifically from the side thereof remote from the intake side 65 of the flange seal 63. The intake-side guide element 111 has two side edges 113 running parallel to one another and a free edge 114. A support portion 115 for the intake-side guide element 111 is provided at a distance from the side edges 113 and extends in each case from the intake-side guide element 111 to the support flange 86. The free end of the support portions 115 is in each case distanced from the free edge 114.

A possible assembly of the housing 31 will be described hereinafter, which is to be considered as particularly advantageous. The sequence of the individual assembly steps can easily be varied according to the marginal conditions present or the adapted variants of the housing 31.

The two shaped part portions 62 and 82 are first connected to form the shaped part 61. The fan 35 is then inserted into the fan receptacle 83. The fan 35 preferably has an intake opening, which, in the inserted state, faces the air passage opening 85 in the base portion 84 of the fan receptacle 83 and is advantageously directly adjacent thereto. As has already been mentioned, the free end of the line portion 70 is connected to the outlet 36 of the fan 35. The fan 35 is then advantageously also wired by means of the cables 37.

The foam inserts 71 and 72 are then inserted in the first housing part 41. The shaped part 61 is then introduced into the first housing part 41 with the intake-side guide element 111 arranged to the fore. In doing so, the shaped part 61 is aligned in such a way that, as it is introduced, the free end region of the intake-side guide element 111 comes to rest in the guide receptacle 76 in the first housing part 41.

The shaped part 61 is inserted into the first housing part 41 until the flange seal 63 contacts the free edge 46 of the first housing part. In doing so, the dome through-openings 64 are penetrated by the fastening domes 47 at the free edge 46 of the first housing part 41 and the encompassing portion 102 on the flange seal 63 comes to rest, in some regions, in the housing recess 49 in the free edge 46 of the first housing part 41. The remaining peripheral portions 101 of the flange seal 63 in this position encompass the other sides of the free edge 46 of the first housing part 41.

The second housing part 51 is then arranged, wherein the free ends of the fastening domes 47 come to rest in the fastening dome recesses 81. The two housing portions 41 and 51 are fixedly interconnected by means of the connecting elements 32. Due to the contact created in the fastening dome recesses 81, it is ensured that the connection between the two housing parts 41 and 51 is sealed by the flange seal 63, but that the flange seal 63 itself is not compressed excessively during the assembly process.

The sound-proofing housing 31 is then ready for installation in a respirator 21.

If the fan 35 is started, air is drawn in thereby through the intake opening 44 into the intake region 33. The drawn-in air flows through the air passage opening 112, past the second shaped part portion 82, and through the intake gap 95 through the air passage opening 85 in the base portion 84 of the device receptacle 83 and into the fan 35. The drawn-in air flows over the device receptacle 83 on the outer side in the region between the flange seal 63 and the support flange 86 before it flows through the intake gap 95 and likewise infiltrates the fan 35 through the air passage opening 85 in the base portion 84 of the device receptacle 83. Before the drawn-in air flows through the air passage opening 112, it flows over the part of the fan that protrudes from the device receptacle 83 (generally a part of the motor of the fan) and thus continuously calls said part. This embodiment of the shaped part 61 advantageously ensures sufficient cooling of the fan 35 and in particular of the motor thereof.

The drawn-in air is compressed in the fan 35 and is guided through the outlet 36 through the line portion 70 and the air passage opening 69 in the flange seal 63 into the delivery region 34 of the housing 31. The compressed air exits the housing 31 through the discharge opening 54 in the base portion 53 of the second housing part 51.

The intake opening 44 and the discharge opening 54 are offset with reference to a central longitudinal axis of the housing 31 and are not arranged over the same axis running parallel to the inner sides of the housing 31.

Due to the guidance of the airflow by means of the guide elements 61 and 111 as well as the arrangement in particular of the air passage openings 69, 85 and 112 as well as the embodiment of the shaped part 61 per se, acoustic emissions occurring during operation of the fan 35 are considerably reduced compared to known solutions. At the same time, the fan is sufficiently cooled and is therefore suitable for a long period of use, which likewise results in a long period of use of the respirator 21.

| List of reference labels | |
|---|---|
| 21 | respirator |
| 22 | touch screen |
| 23 | housing |
| 24 | connecting piece |
| 31 | housing |
| 32 | connecting element |
| 33 | intake region |
| 34 | delivery region |
| 35 | fan |
| 36 | outlet of 35 |
| 37 | cable |
| 41 | first housing part |
| 42 | indentation of 41 |
| 43 | base portion of 41 |
| 44 | intake opening |
| 45 | sleeve portion at 44 |

List of reference labels

| | |
|---|---|
| 46 | free edge of 41 |
| 47 | fastening dome |
| 48 | through-opening in 47 |
| 49 | housing recess |
| 50 | side wall of 41 |
| 51 | second housing part |
| 52 | indentation of 51 |
| 53 | base portion of 51 |
| 54 | discharge opening |
| 55 | collar at 54 |
| 56 | relief opening |
| 57 | pressure relief valve |
| 58 | free edge of 51 |
| 59 | reinforcing rib |
| 61 | shaped part |
| 62 | first shaped part portion |
| 63 | flange seal |
| 64 | dome through-opening |
| 65 | intake side of 63 |
| 66 | delivery side of 63 |
| 67 | delivery-side guide element |
| 68 | support portion for 67 |
| 69 | air passage opening |
| 70 | line portion |
| 71 | foam insert |
| 72 | foam insert |
| 76 | guide receptacle |
| 77 | rib |
| 78 | retaining tab |
| 80 | through-opening in 81 |
| 81 | fastening dome recess |
| 82 | second shaped part portion |
| 83 | fan receptacle |
| 84 | base portion of 83 |
| 85 | air passage opening |
| 86 | support flange |
| 87 | lip seal |
| 88 | recess of 86 |
| 89 | cable through-opening in 86 |
| 90 | side edge of 86 |
| 92 | fixing device |
| 93 | fixing cam receptacles |
| 94 | fixing cams |
| 95 | intake gap |
| 96 | support element |
| 97 | retaining cam |
| 98 | deflected portion of 96 |
| 101 | encompassing portion |
| 102 | encompassing portion |
| 103 | guide portion |
| 104 | cable through-opening in 102 |
| 105 | guide through-opening |
| 111 | intake-side guide element |
| 112 | air passage opening in 111 |
| 113 | side edge of 111 |
| 114 | free edge of 111 |
| 115 | support portion |
| 116 | membrane |

What is claimed is:

1. A sound-proofing housing for a respirator comprising:
a first housing part;
said first housing part having an intake opening permitting entry of air into said housing;
a fan arranged in said housing to draw in air;
a second housing part;
said second housing part having a discharge opening;
a shaped part arranged in said housing, said shaped part forming a flange seal resting between said first and second housing parts;
an intake region in said housing;
a delivery region in said housing;
said shaped part dividing said housing into said intake and delivery regions;
said flange seal having an intake side facing said intake region;
a fan receptacle configured to hold said fan, said fan receptacle protruding from said intake side of said flange seal, said fan receptacle having a free end;
air guides configured to guide air drawn at least through said flange seal into said delivery region of said housing by said fan;
a support flange, said support flange having at least one air passage opening, said support flange having contact sides contacting inside said housing, said support flange being provided in a region of the free end of said fan receptacle; and,
at least one further air passage opening for air drawn in by said fan, said at least one further air passage opening being provided in said fan receptacle adjacent to said flange seal intake side.

2. The sound-proofing housing for a respirator as claimed in claim 1 further comprising:
lip seals provided on said support flange contact sides.

3. The sound-proofing housing for a respirator as claimed in claim 1 further comprising:
an intake-side guide element protruding from said support flange, said intake-side guide element having at least one respective air passage opening.

4. The sound-proofing housing for a respirator as claimed in claim 3 further comprising:
said intake-side guide element is providing a support portion extending between said intake-side air guide and said support flange.

5. The sound-proofing housing for a respirator as claimed in claim 3 further comprising:
a guide receptacle receiving at least a portion of said intake-side guide element, said guide receptacle resting in the same housing part as saidintake-side guide element.

6. The sound-proofing housing for a respirator as claimed in claim 1 further comprising:
a respective one of said first and second housing parts includes at least one fastening dome, said at least one fastening dome protruding from a free edge of said respective one of said first and second housing parts;
the respective other one of said first and second housing parts including at least one fastening dome recess configured to receive said at least one fastening dome; and,
a stop for said at least one fastening dome, said stop being provided in said fastening dome recess to define spacing between assembled first and second housing parts.

7. The sound-proofing housing for a respirator as claimed in claim 6 further comprising:
a dome through-opening in said flange seal, said dome through-opening being peripherally closed.

8. The sound-proofing housing for a respirator as claimed in claim 1 further comprising:
a delivery-side guide element, said delivery-side guide element protruding from a delivery side of said flange seal; and,
at least one support portion for said delivery-side guide element extending from said delivery-side guide element to said flange seal.

9. The sound-proofing housing for a respirator as claimed in claim 1 further comprising:
at least one cable through-opening provided in said flange seal, said at least one cable through-opening being provided in an encompassing portion protruding from said flange seal;

a housing recess configured to receive at least a portion of said encompassing portion, said housing recess being provided in the same housing part as said encompassing portion of said flange seal.

10. The sound-proofing housing for a respirator as claimed in claim 1 further comprising:
   at least one cable through-opening provided in said support flange.

11. The sound-proofing housing for a respirator as claimed in claim 3 further comprising:
   at least one cable through-opening provided in said intake-side guide element.

12. The sound-proofing housing for a respirator as claimed in claim 1 further comprising:
   an air passage opening provided in said flange seal; and,
   a guide portion, said guide portion connecting said air passage opening of said flange seal to a delivery-side outlet of said fan.

13. The sound-proofing housing for a respirator as claimed in claim 1 further comprising:
   a flange seal support arranged on said intake side of said flange seal.

14. The sound-proofing housing for a respirator as claimed in claim 1 further comprising:
   said shaped part including a first portion that includes said flange seal, said shaped part including a second portion that includes said fan receptacle; and,
   a fixing device configured to connect said shaped part first portion to said shaped part second portion.

15. The sound-proofing housing for a respirator as claimed in claim 14 further comprising:
   said fixing device including at least one fixing cam provided on said second portions of said shaped part, said fixing device also including at least one fixing cam receptacle provided on said first portions of said shaped part; and,
   said fixing device providing at least some spacing between said first and second portions in assembly, an intake gap being formed by said spacing, said intake gap having the form of at least one additional air passage opening.

16. A sound-proofing housing for a respirator comprising:
   a first housing part;
   said first housing part having an intake opening permitting entry of air into said housing;
   a fan arranged in said housing to draw in air;
   a second housing part;
   said second housing part having a discharge opening;
   a shaped part arranged in said housing, said shaped part forming a flange seal resting between said first and second housing parts;
   an intake region in said housing;
   a delivery region in said housing;
   said shaped part dividing said housing into said intake and delivery regions;
   said flange seal having an intake side facing said intake region;
   a fan receptacle configured to hold said fan, said fan receptacle protruding from said intake side of said flange seal, said fan receptacle having a free end;
   air guides configured to guide air drawn at least through said flange seal into said delivery region of said housing by said fan;
   a support flange, said support flange having at least one air passage opening, said support flange having contact sides contacting inside said housing, said support flange being provided in a region of the free end of said fan receptacle;
   at least one further air passage opening for air drawn in by said fan, said at least one further air passage opening being provided in said fan receptacle adjacent to said flange seal intake side; and,
   an intake-side guide element protruding from said support flange.

17. The sound-proofing housing for a respirator as claimed in claim 16 further comprising:
   said intake-side guide element is providing a support portion extending between said intake-side guide element and said support flange.

18. The sound-proofing housing for a respirator as claimed in claim 16 further comprising:
   a guide receptacle receiving at least a portion of said intake-side guide element, said guide receptacle resting in the same housing part as said intake-side guide element.

19. The sound-proofing housing for a respirator as claimed in claim 16 further comprising:
   a delivery-side guide element, said delivery-side guide element protruding from a delivery side of said flange seal; and,
   at least one support portion for said delivery-side guide element extending from said delivery-side guide element to said flange seal.

20. The sound-proofing housing for a respirator as claimed in claim 16 further comprising:
   said shaped part including a first portion that includes said flange seal, said shaped part including a second portion that includes said fan receptacle; and,
   a fixing device configured to connect said shaped part first portion to said shaped part second portion.

21. A sound-proofing housing for a respirator, said sound-proofing housing comprising:
   a first housing part having an intake opening for entry of air into said sound-proofing housing, air being drawn in by a fan arranged in said sound-proofing housing;
   a second housing part having a discharge opening for discharge of drawn-in air from said sound-proofing housing;
   a shaped part arranged in said sound-proofing housing, said shaped part forming a flange seal, said flange seal is sandwiched between said first housing part and said second housing part, said shaped part dividing said sound-proofing housing into an intake region and a delivery region;
   a fan receptacle for holding said fan in said sound-proofing housing, said fan receptacle protruding from an intake side of said flange seal facing said intake region, said fan receptacle including an air passage opening for air drawn by said fan, said air passage opening being disposed adjacent to said intake side of said flange seal;
   a support flange provided in a region of a free end of said fan receptacle, said support flange including contact sides in contact with an inner side of said first housing part and a non-contact side not in contact with said inner side of said first housing part when the housing is put together; and
   an intake-side guide element including a second air passage opening for air drawn in by said fan, said intake-side guide element protruding from a side of said support flange, said side is remote from said intake side of said flange seal, said intake-side guide element is adjacent to said non-contact side of said support flange, wherein air drawn by said fan entering through said intake opening passes through said air passage opening of said intake-side guide element, then between said non-contact side of said support flange and said first housing part, and then through said air passage opening of said fan receptacle.

22. The sound-proofing housing according to claim 21, further comprising seal elements on said contact sides of said support flange.

23. The sound-proofing housing according to claim 21, further comprising at least one support portion for said intake-side guide element, said at least one support portion extending from said intake-side guide element to said support flange.

24. The sound-proofing housing according to claim 21, further comprising at least one guide receptacle for receiving a portion of said intake-side guide element in said first housing part.

25. The sound-proofing housing according to claim 21, wherein said first housing part including at least one fastening dome, said at least one fastening dome protruding from a free edge of said first housing part, and said second housing part including at least one fastening dome recess for receiving said at least one fastening dome, said fastening dome recess having a stop for said at least one fastening dome to ensure a defined spacing between housing parts when said sound-proofing housing is put together.

26. The sound-proofing housing according to claim 25, further including at least one dome through-opening in said flange seal for passage of said at least one fastening dome, said at least one dome through-opening being peripherally closed.

27. The sound-proofing housing according to claim 21, further comprising
 a delivery-side guide element in a form of a further air-guiding device on said flange seal, said delivery-side guide element protruding from a delivery side of said flange seal, which is arranged opposite said intake side of said flange seal, and
 at least one support portion for said delivery-side guide element, said at least one support portion for said delivery-side guide element extending from said delivery-side guide element to said flange seal.

28. The sound-proofing housing according to claim 21, further comprising:
 at least one cable through-opening in said flange seal for passage of cables to wire said fan, said at least one cable through-opening being provided in an encompassing portion, which protrudes from said flange seal, and
 a housing recess for receiving at least a region of said encompassing portion in said first housing part in which said encompassing portion comes to rest when the sound-proofing housing is put together.

29. The sound-proofing housing according to claim 21, further comprising at least one cable through-opening in said support flange for passage of cables to wire said fan.

30. The sound-proofing housing according to claim 21, further comprising at least one cable through-opening for passage of cables to wire said fan in said support flange and/or in said intake-side guide element.

31. The sound-proofing housing according to claim 21, further comprising:
 at least one air passage opening in said flange seal, said at least one air passage opening is spaced from an edge of said flange seal, and
 a guide portion, which connects said at least one air passage opening to a delivery-side outlet of said fan.

32. The sound-proofing housing according to claim 21, further comprising a support element to support said flange seal, said support element is located on said intake side of said flange seal.

33. The sound-proofing housing according to claim 21, wherein said shaped part including at least two parts:
 a first shaped part portion having at least said flange seal, and
 at least one further shaped part portion having at least said fan receptacle, and a fixing device for connecting said first shaped part portion to said at least one further shaped part portion.

34. The sound-proofing housing according to claim 33, wherein said fixing device including:
 at least one fixing cam provided on one of said shaped part portions, and
 at least one fixing cam receptacle provided on another of said shaped part portion, said at least one fixing cam being fixable in said at least one fixing cam receptacle, said fixing device being formed in such way that, when said shaped part portions have been joined, they are spaced from each other, at least in a one area, so that an intake gap for air drawn in by said fan is maintained in a form of at least one further air passage opening.

* * * * *